United States Patent [19]

Darkwa et al.

[11] Patent Number: 5,077,042

[45] Date of Patent: Dec. 31, 1991

[54] CONDITIONING HAIR RELAXER SYSTEM WITH CONDITIONING ACTIVATOR

[75] Inventors: Adu G. Darkwa; Florine Newell, both of Chicago, Ill.

[73] Assignee: Johnson Products Co., Inc., Chicago, Ill.

[21] Appl. No.: 410,803

[22] Filed: Sep. 22, 1989

Related U.S. Application Data

[63] Continuation-in-part of Ser. No. 399,385, Aug. 25, 1989, Pat. No. 4,950,485, which is a continuation of Ser. No. 173,318, Mar. 25, 1988, abandoned.

[51] Int. Cl.$^5$ .......................... A61K 7/09; A45D 7/04
[52] U.S. Cl. .................................... 424/071; 132/203; 514/946
[58] Field of Search .................... 424/71, 78; 132/202, 132/203; 514/947, 946

[56] References Cited

U.S. PATENT DOCUMENTS

| | | | |
|---|---|---|---|
| 3,017,328 | 1/1962 | Chidrey et al. | 167/87.1 |
| 3,923,668 | 12/1975 | Johnston | 252/16 |
| 4,175,572 | 11/1979 | Hsiung et al. | 132/7 |
| 4,237,910 | 12/1980 | Khalil et al. | 132/202 |
| 4,304,244 | 12/1981 | de la Guardia et al. | 132/7 |
| 4,390,033 | 6/1983 | Khalil et al. | 132/7 |
| 4,416,296 | 11/1983 | Meyers | 132/7 |
| 4,524,787 | 6/1985 | Khalil et al. | 132/7 |
| 4,579,131 | 4/1986 | Syed | 132/7 |
| 4,602,648 | 7/1986 | Syed et al. | 424/70 X |
| 4,605,018 | 8/1986 | de la Guardia et al. | 132/7 |

FOREIGN PATENT DOCUMENTS 2141454 6/1984 United Kingdom .

OTHER PUBLICATIONS

Miranol, Inc. Ethnic Formulary, product literature, pl. 9 (Feb. 21, 1985).
Miranol Chemical Company, Inc., Miranol Products for Cosmetics Toiletries, pp. 25–26 (1985).
"Hair Treatment Products Formulary," *Cosm. & Toilet,* 100, 77, 82 (Apr.), 1985.
Harris, R., "Hair Relaxing," *Cosm. & Toilet,* 94 51–56 (Apr.) 1979.
DeNavarre M., *The Chemistry and Manufacture of Cosmetics,* 2nd Edition, vol. IV, Chap. 59, pp. 1155, 1159, 1165, Continental Press, Orlando, Fla. (1975).
Balsam, et al., *Cosmetics Science and Technology;* Second Edition, vol. 2, Ch. 22, pp. 251, 264–267, 277 Wiley-Interscience (1972).

*Primary Examiner*—Thurman K. Page
*Assistant Examiner*—Susan S. Rucker
*Attorney, Agent, or Firm*—Olson & Hierl

[57] ABSTRACT

A conditioning activator for a no-lye hair relaxer and a conditioning hair relaxer system includes a conditioning agent which is a water-soluble cationic compound. In a preferred embodiment the cationic conditioning agent is a cationic polymer. Also disclosed are methods for preparing phase-stable no-lye cream bases suitable for conditioning hair relaxer systems.

46 Claims, No Drawings

CONDITIONING HAIR RELAXER SYSTEM WITH CONDITIONING ACTIVATOR

CROSS-REFERENCE TO RELATED APPLICATION

This application is a continuation-in-part of our prior application titled "Hair Relaxer Cream," Ser. No. 399,385, filed Aug. 25, 1989, now U.S. Pat. No. 4,950,485, which is a continuation of Ser. No. 173,318, filed Mar. 25, 1988, now abandoned.

TECHNICAL FIELD

This invention relates to the straightening or relaxing of hair, and in particular to highly alkaline conditioning hair relaxer systems.

BACKGROUND ART

Aqueous highly alkaline hair relaxing or straightening compositions are known in the art. These compositions usually have a highly alkaline pH, i.e., a pH of about 12 to about 14, due to the presence of an alkaline hair relaxing material. For example, a water-soluble inorganic lye or non-lye caustic base, such as alkali or alkaline earth hydroxide or a relatively strong organic base such as guanidine, guanidine hydroxide or quaternary ammonium hydroxide is used.

Aside from their causticity, one principal disadvantage of highly alkaline hair relaxers is that they leave the hair in a brittle state and harsh to the touch. Another disadvantage is that highly alkaline compositions containing all or a portion of the active alkaline hair relaxing agent are difficult to compound in the form of phase-stable emulsified creams. This instability limits the effective inclusion of useful hair conditioning agents. Thus, there is a long-standing need and desire for a conditioning hair relaxing system.

Modern highly alkaline hair relaxers are preferably of the type commonly called "no-base" hair relaxers. The term "no-base" means that the scalp need not be coated with a protective oleaginous base such as petrolatum, mineral oil and lanolin, before applying the highly alkaline hair relaxer.

One type of no-base hair relaxer formulation contains as the sole active hair straightening agent an alkali metal hydroxide, typically a caustic base, such as sodium hydroxide, potassium hydroxide or lithium hydroxide. When a relatively low active level of about 1.5 to about 2.5 weight percent of caustic base is used, the protective base is applied only to the hairline to protect the skin around the forehead, ears and neckline. Such no-base formulations have some of the protective oleaginous material emulsified in an aqueous composition, preferably in the form of a viscous cream, and are supplied in a "single product" kit.

Another no-base hair relaxer formulation is commonly called a "no-lye" hair relaxer. With a no-base, no-lye relaxer, a protective base need not be applied to the scalp and may not need to be applied to the hairline. The term "no-lye" as used herein means that the active hair straightening agent is an organic chemical base instead of inorganic caustic base. In commercial practice, the relatively strong organic chemical base, guanidine is usually present in the form of guanidine hydroxide. However, guanidine hydroxide is not generally stable for long periods in aqueous solutions. Consequently, it must be prepared fresh just before using.

Guanidine hydroxide is generally prepared by reacting an inorganic chemical base such as an alkaline earth hydroxide with an aqueous solution of a salt of the strong organic chemical base guanidine where the anion of this salt is capable of being precipitated by the cation of the alkaline earth hydroxide. In commercially available products of this type, the guanidine hydroxide is generally prepared using guanidine carbonate and calcium hydroxide.

When such a no-lye hair relaxer is commercially used, the product is supplied as a two-part kit. One part contains the guanidine carbonate in substantially liquid form and is commonly called the "activator." The other part contains relatively high amounts of about 4 to about 7 percent calcium hydroxide emulsified in a cosmetic cream base. Prior to using, the consumer or beautician mixes the cream and activator portions of the kit together. The resulting no-lye hair relaxer is then relatively promptly (preferably within 24 hours) applied to the hair.

Some great strides have been made in formulating no-base hair relaxer compositions by incorporating conditioning agents in the highly alkaline emulsions so that the straightened hair has a better feel after such a treatment. However, highly alkaline emulsion products containing sufficient inorganic alkaline material to provide all or a portion of the active hair relaxing agent, as well as conditioning agent, are difficult to compound. These emulsions require much care particularly during preparation on a commercial scale, and separate or de-emulsify relatively quickly on ageing thereby limiting their commercially useful lifetime.

Most no-base hair relaxer cream products are preferably aqueous emulsions in which water is the continuous phase, i.e., oil-in-water emulsions, because they are easier to rinse from the hair. Instability or de-emulsification results in a destabilized cream product having two distinctly visible phases. While such destabilized cream products may be used, they must be remixed before using in an attempt to assure the user that the active ingredients are at the proper levels in the portion being used. However, such mixing, even though done thoroughly by hand, does not, in fact, give the user consistent results with such products. Improper mixing can also cause skin irritation or result in increased hair breakage. Product destabilization and resulting consumer dissatisfaction are among the chief complaints in the industry. Thus, a phase-stable cream is needed that shows substantially no visible separation into distinct phases on storage aging.

Cationic compounds, in particular, are generally considered to improve the condition of hair. The terms "cationic conditioning agent" and "cationic conditioner" as used herein refer to substantially water-soluble cationic compounds which under certain circumstances are substantive to hair. It is commonly recognized that substantive cationic conditioning compounds can effectively leave the hair feeling silky, soft and more manageable with less static fly-away, characteristics which are desirable attributes of hair conditioners.

During a hair-relaxation treatment, the hair can be most easily penetrated by a cationic conditioner present in the relaxer. The hair is swollen during relaxation, under the action of the alkali, and the cuticles on each hair shaft are sufficiently raised so that the conditioner can find entry between them into the hair shaft. In contrast, after the relaxer is rinsed off, the hair deswells and the cuticles flatten. Conditioners applied at this stage to the deswollen hair cannot penetrate the hair shafts to the same extent and are less effective in achieving conditioning.

Most of the strongly alkaline hair relaxers for home use are sold in kits containing one or more conditioners packaged in a separate containers for application to the hair either before applying the relaxer or after the relaxation process. Such conditioning, performed as a separate step, is inconvenient and is only partially effective in overcoming the harshness imparted by the alkaline treatment. The inclusion of water-soluble polymeric cationic compounds into a strongly alkaline hair relaxer composition is particularly desirable to counteract the harshness imparted by the alkalinity. However, some water-soluble cationic polymers are not useful ingredients for strongly alkaline compositions. Some water-soluble cationic polymers, when incorporated into strongly alkaline emulsion cream compositions, especially in the pH range from about 12.5 to about 13.8, can cause phase destabilization of the emulsion during storage aging. Other water-soluble cationic polymers which do not destabilize the emulsion may, nevertheless, lose their own effectiveness to condition hair under the highly alkaline pH required for relaxation.

Until now, some success in achieving a conditioning hair-relaxer system was met by incorporating certain useful water-soluble polymeric quaternary nitrogen conditioning agents useful as a component of the highly alkaline no-lye cream base portion of a two-product kit. For example, the use of a quaternary nitrogen-containing polymer prepared by polymerizing and co-polymerizing a diallyldimethylammonium salt is disclosed in co-assigned U.S. Pat. Nos. 4,175,572 ('572), 4,237,910 ('910), 4,390,033 ('033), 4,524,787 ('787) and in co-assigned co-pending U.S. patent application Ser. No. 173,318, abandoned in favor of filing continuation application Ser. No. 399,385, now issued as U.S. Pat. No. 4,950,485. The disclosures of each of the foregoing are incorporated herein by reference. Another useful water-soluble quaternary nitrogen polymer, a copolymer of methylvinylimidazolium chloride and vinylpyrrolidone, is disclosed in co-assigned U.S. patent application Ser. No. 763,519 and related French Patent publication No. 2,585,947A, both now abandoned, the disclosures of which are also incorporated herein by reference.

Problems of product instability are also caused by the presence of relatively high amounts of water-insoluble oleaginous ingredients which must be co-emulsified with the alkaline material. Oleaginous materials, such as petrolatum and lanolin, are desirable in no-lye cosmetic cream bases to maintain the benefits of a no-base procedure. But the water-insoluble character of these materials greatly decreases the chances of successfully formulating a phase-stable cream, especially a highly alkaline cream containing inorganic alkaline material. These problems are magnified when a formula is scaled up for the production of commercial quantities.

Part of the foregoing problems were also overcome in the previously mentioned '033 and '910 patents of our assignee, by using certain lipophilic organically-modified hectorite clay gellants. Those clay gellants were disclosed for stabilizing highly alkaline no-base hair relaxer compositions containing relatively high amounts of oleaginous material against phase separation. Commercial hair relaxer products embodying the principles disclosed in these patents have been marketed. However, compounding a phase-stable cream, even with the above disclosed hectorite clay gellant, requires considerable care to substantially uniformly disperse the disclosed hectorite clay gellant.

Moveover, relatively high amounts (about 8 to about 12 weight percent) of the hectorite clay gellant are generally required to achieve a relatively stiff viscous cream. For example, the '033, the '910 and the '572 patents all disclosed that at below about 2 weight percent of the hectorite clay gellant, little phase stability improvement was noted and the resulting creams were relatively soft. Thus, while generally elegant, relatively stiff viscous creams can be obtained by practicing the emulsion stabilizing principles taught in the '033 and '910 patents, the products are relatively costly to manufacture commercially from the standpoints of costs for labor, materials and energy.

No-base hair relaxers are desirably formulated as emulsified viscous creams so that once applied to the user's hair, they will not drip onto the skin or into the eyes of the person receiving a hair straightening procedure. The cosmetic cream base portion of a no-lye hair relaxer kit must also mix easily with the liquid activator portion without thinning to a soft runny cream.

A commercially desirable conditioning hair-relaxing system, therefore, would utilize a phase-stable, viscous no-base hair relaxer cream, effect conditioning while relaxing the hair, be easy to remove from the hair at the end of the straightening or relaxer procedure and provide a substantive conditioned effect to the relaxed hair.

The present invention provides for such a conditioning hair-relaxing system characterized by a conditioning activator for a no-base, no-lye hair relaxer, and for a phase-stable viscous cosmetic cream base for use therewith in no-base hair relaxer systems and methods of preparing same.

SUMMARY OF THE INVENTION

An aqueous conditioning activator for use in a no-base, no-lye hair relaxer system is disclosed. The conditioning activator is substantially liquid and comprises, prior to mixing with a no-lye cream base, a water solution of effective amounts each of a water-soluble organic salt of a relatively strong organic base having an anion capable of being precipitated by an alkaline earth metal ion under highly alkaline conditions and a cationic conditioning agent. A conditioning activator of this invention contains all or a portion of the conditioning agent desired in a conditioning hair relaxer system.

As used herein, the term "effective amount" with regard to the organic salt means that when the activator of this invention is mixed with a no-lye cream base, sufficient organic base is released in the admixture to provide an active hair relaxing agent. With reference to the conditioning agent in the admixture, the term "effective amount" means that a sufficient amount of conditioning agent is present to either effect conditioning during the relaxation process or to produce a conditioned effect on the relaxed hair when the relaxation process is completed and the hair relaxer is removed by rinsing with water, or in both steps.

In a particularly preferred embodiment of a conditioning activator, the cationic conditioning agent is a quaternary nitrogen polymer or copolymer derived from polydiallyldimethylammonium chloride, and the water-soluble organic salt is guanidine carbonate. For use, this activator is mixed with a no-lye cream base to provide a conditioning hair relaxer system. In one surprising aspect, it was found that by including this useful cationic polymer in a substantially liquid activator, instead of in the cream base, lesser amounts effectively conditioned the relaxed hair. Preferably, a conditioning activator of this invention is mixed with a highly alkaline no-base, no-lye cosmetic cream base containing calcium hydroxide which is phase stable and retains its viscosity on storage aging.

The term "phase-stable", as used herein, means that on storage aging the highly alkaline emulsion of the cosmetic cream base does not de-emulsify, i.e., substantially no separation of the emulsion into distinct phases is visible over a relatively long commercially useful lifetime in the container or jar. The term "commercially useful lifetime" means that no separation of the emulsion into distinct phases is visible after storage aging for at least about one week upon accelerated ageing at an elevated temperature of about 45 degrees C. (about 113 degrees F.) or for at least about four weeks at ambient room temperature and preferably at least about 3 months.

A phase-stable cosmetic cream base of this invention can be prepared as an oil-in-water emulsion by the methods disclosed herein. A sufficient amount of nonvolatile inorganic alkaline material is dissolved in the continuous water phase both to provide a highly alkaline pH of about 12 to about 14 in the final hair relaxer and all or a portion of the hair-relaxing agent.

Surprisingly, useful stiff, viscous, phase-stable highly-alkaline creams are achieved with relatively low amounts of non-water components, preferably making up no more than 50 weight percent based on the total weight of the composition calculated on a dry solids basis. More surprisingly, such highly-alkaline creams which are phase-stable on storage aging can be prepared at amounts of the phase-stabilizing hectorite clay gellants taught in the '033 and '910 patents discussed earlier which ordinarily produced relatively soft creams with little stability improvement. Further surprisingly, substantially stiff, viscous phase-stable, highly-alkaline creams are achieved by practicing the principles of the methods of this invention even in the absence of the foregoing clay gellants.

Briefly described, the non-water components in a phase-stable cosmetic cream base composition of this invention comprise, in addition to the alkaline material, a lipophilic oleaginous material, a primary emulsifier that is a nonionic emulsifier comprising a mixture of fatty alcohols having about 12 to about 24 carbon atoms in the fatty carbon chain; an auxiliary emulsifier comprising a hydrophilic nonionic emulsifier, an anionic emulsifier, and an amphoteric or zwitterionic emulsifier; and a polyhydroxy compound having about 3 to about 6 carbon atoms. Additionally, the non-water components can include a polymeric conditioning agent and a relative low amount of a lipophilic modified hectorite clay gellant (preferably up to about 2 weight percent) of the type disclosed in the '033, '910 and '572 patents. No-lye cream bases which contain polymeric conditioning agent, however, are usually mixed with non-conditioning activator, i.e., containing no conditioning agent, but can be mixed with a conditioning activator if extra conditioning is desired.

One preferred no-base, no-lye conditioning hair-relaxer system is prepared by converting a no-base, no-lye cream base to a hair relaxer by mixing about 3.6 parts by weight of a cream base containing about 4 to about 7 weight percent calcium hydroxide with one art by weight of conditioning activator. Preferably the conditioning activator, prior to mixing, comprises about 25 to about 30 weight percent guanidine carbonate, and sufficient cationic conditioning agent to provide about 0.01 to about 5 weight percent, dry solids basis, in the hair relaxer admixture. Preferably the conditioning activator comprises a thickened vehicle also containing a polyhydroxy compound having 3 to about 6 carbon atoms.

One benefit of a conditioning activator as disclosed is that a conditioning hair relaxer system can be prepared by converting a no-base no-lye cream base which does not ordinarily condition the hair into a useful conditioning hair relaxer. A substantially liquid conditioning activator also overcomes the attendant instability problems that can arise when the conditioning agent is a component of the cream base portion, yet retains the maximizing benefit of conditioning of hair during the relaxation process.

In one particular advantage, a substantive conditioning effect can be produced on the relaxed hair with less cationic conditioning agent than is required when the same cationic agent is incorporated as a component of the cream base.

Another benefit of preparing a conditioning hair-relaxing system by admixture of a substantially liquid conditioning activator with a phase-stable cosmetic cream base prepared according to the principles of this invention is that problems leading to skin irritation and uneven hair relaxation due to inconsistent distribution of actives are substantially overcome. Another advantage is that a phase-stable viscous cream base and conditioning activator suitable for use in preparing a conditioning no-base no-lye hair relaxer system each can be economically and easily prepared on a commercial scale.

Still further advantages and benefits will be apparent to those skilled in the art from the description, examples and claims which follow.

DETAILED DESCRIPTION OF THE INVENTION

This invention relates to substantially liquid conditioning activators for no-lye hair relaxer systems, and in particular for no-base, no-lye conditioning hair relaxer systems. The invention also relates to phase-stable highly alkaline cosmetic cream bases which are relatively stiff viscous creams and to methods for preparing these cream bases.

For convenience, the term "no-lye cream base" as used herein refers to the cosmetic cream base portion of a hair relaxer kit containing inorganic alkaline material with an alkaline earth cation, such as alkaline earth oxide or alkaline earth hydroxide. The term "no-lye hair relaxer" refers to the resulting admixture of the foregoing no-lye cream base and activator. The terms, "no-base hair relaxer cream" or "hair relaxer", refers generally to a highly alkaline hair straightening product whether supplied in a kit as a single product, such as a lye-type, or as two-products, such as a no-lye type, for use as a hair-relaxer system.

The term "activator" and "non-conditioning activator" means a water solution of a salt of a relatively strong organic base with an anion capable of being precipitated by an alkaline earth metal ion under alkaline conditions. The term "conditioning activator" means an activator as previously defined containing a water-soluble cationic compound.

A no-base, no-lye hair relaxer preferably contains as the active hair-relaxing agent, a water-soluble alkaline caustic material that is preferably a strong organic base, such as guanidine or guanidine hydroxide. For this purpose, either the emulsified cream base portion or the activator portion may contain a water-soluble salt of a strong organic base with an anion capable of being precipitated by an alkaline earth metal ion under highly alkaline conditions.

In this embodiment, the organic base is released in sufficient amount to relax hair just before use by the reaction of guanidine carbonate with calcium hydroxide. For this purpose, calcium hydroxide is usually emulsified in a no-lye cream base, and guanidine carbonate is present in a separate aqueous activator solution. The activator is combined with the emulsion to form the hair relaxer just before application of the hair relaxer to the hair. Alternatively, the guanidine carbonate could be included in the emulsion and calcium hydroxide in an aqueous suspension added just before use, but this approach is impractical. The amount of calcium hydroxide required for the reaction would be difficult to suspend in substantially liquid form and would likely result in a non-uniform reaction mixture which would not relax the hair properly.

In commercial practice, the preferred water-soluble salt of a strong organic base is usually guanidine carbonate and preferably is present in the activator portion of a two-product kit in substantially liquid form.

The amount of guanidine in the final composition is generally about 0.05 to about 0.8 molar, preferably about 0.4 to about 0.6 molar. Guanidine concentrations within this range are obtained from guanidine carbonate concentrations in the final hair relaxer mixture between about 0.031 and about 0.38 molar and calcium hydroxide concentrations in the final mixture between about 0.025 and about 2.2 molar. In the emulsified composition prior to the addition of aqueous guanidine carbonate, the amount of calcium hydroxide is generally between about 0.1 and about 10 weight percent, and preferably between about 4 and about 7 weight percent.

Reference to weight percent throughout this specification is based on the dry solids weight percent of the individual ingredient present with reference to the total weight of the cream composition, the activator composition or the hair relaxer resulting from the admixture of the two as indicated.

Other organic bases which may be used in place of guanidine, include N-methyl guanidine, dimethylaminoguanidine (sym. and asym.), acetamidine, dimethylaminoamidine, aminoamidine and acetamide. The organic base may be liberated from salts other than the carbonate salt, such as from a sulfate or sulfite, fluoride, oxalate, tartrate, laurate or alginate salt.

Other alkaline earth hydroxides, such as barium or strontium hydroxide may be used in place of calcium hydroxide to release free guanidine base from guanidine salt. Alkaline earth oxides may also be used, producing hydroxides when added to water.

It has now been found that effective amounts of cationic conditioning agent can be included as components of a substantially liquid activator for use in a no-base, no-lye hair relaxer system. For purposes of illustrating a conditioning activator, and not by way of limitation, remarks hereafter will refer to guanidine carbonate as the salt from which the organic base, guanidine, is released by reacting with calcium hydroxide since these are the materials of most commercial interest.

A cationic compound useful as a cationic conditioning agent in an activator can include water-soluble non-polymeric quaternary ammonium compounds, quaternized cationic polymers with at least one available positively charged quaternary nitrogen atom in each periodically repeating unit of the polymer chain and copolymers thereof, and unquaternized polymers having tertiary amino nitrogen groups that become quaternized when protonated under alkaline conditions and corresponding copolymers thereof. The choice of cationic compound is limited only by its solubility and its ability to effect conditioning during the relaxation process or to produce a substantive conditioned effect on the relaxed hair, so long as it does not interfere with the liberation of the active hair relaxing agent.

It is generally recognized that conditioning is commonly judged subjectively by the user of a hair relaxer. Where conditioning is effected during the relaxation process, a substantive conditioned effect may be observed subjectively as improved tactile characteristics of the hair during and following the removal of the hair relaxer over those same characteristics normally observed in the absence of such conditioning.

The term "conditioned effect" is used herein in its commonly understood meaning of improvements such as easier combing of the wet or dry hair, increased luster, a silkier, smoother and softer tactile feel on the hair, more manageable setting and styling and the like. The term "substantive conditioned effect" encompasses one or more of the foregoing desirable characteristics which may be either apparent by a visual or tactile inspection of the relaxed hair as well as characteristics which may only be measured objectively. For example, changes in the measured tensile strength of the relaxed hair or microscopically visible changes in the hair's structure attributable to the presence of the cationic conditioning agent can show beneficial protective conditioning during the relaxation process. For example, less loss of hair from breakage, less splitting of the relaxed fibers and like desirable characteristics are associated with protective conditioning of hair against the deleterious action of the caustic materials.

Preferably the water-soluble cationic conditioning agent is a cationic compound which retains a cationic positive charge at a pH above at least 8, more preferably at above about pH 9. The amount of water-soluble cationic conditioning agent present in the activator, prior to admixture with a no-lye cream base can be about 0.05 to about 15 weight percent, preferably about 0.1 to about 10 weight percent, calculated on a dry solids basis of the total weight of the activator composition. The actual amount used can be greater and is limited only by the solubility and cost of the cationic conditioning agent and the amount of conditioning effect desired. Preferably the cationic conditioning agent is present in an amount sufficient to provide about 0.01 to about 5 weight percent, preferably about 0.05 to about 1.5 weight percent more preferably about 0.1 to about 1 weight percent, calculated on a dry solids basis of the total weight of the hair relaxer admixture.

Quaternized polymeric cationic conditioning agents are particularly preferred, and for convenience are referred to hereafter simply as cationic polymers. Particularly preferred are quaternary nitrogen polymers prepared by the polymerization of a dialkyldiallylammonium salt or copolymer thereof in which the alkyl group contains 1 to about 18 carbon atoms, and more preferably where the alkyl group is methyl or ethyl.

Details concerning the preparation of these polymers can be found in U.S. Pat. No.'s 3,288,770, 3,412,019 and 4,772,462, the pertinent disclosures of which are incorporated herein by reference.

For example, cationic homopolymers and copolymers of polydiallyldimethylammonium chloride are available in aqueous compositions sold under the trademark MERQUAT by the Calgon Corporation, subsidiary of Merck & Co., Pittsburgh, Pa. The homopolymer, which is named Polyquaternium-6 in the *CTFA Cosmetic Ingredient Dictionary*, 3rd Ed., published in 1982 by the Cosmetic Toiletry and Fragrance Association, Inc. (hereafter CTFA Dictionary and CTFA name), is sold under the trademark MERQUAT-100, and is described as having a weight average molecular weight of approximately 100,000. A copolymer reaction product of dimethyldiallylammonium chloride with acrylamide monomers is named Polyquaternium-7 in the CTFA Dictionary, is described as having a weight average molecular weight of approximately 500,000 and is sold under the trademark MERQUAT-550. Another copolymer reaction product of dimethyldiallylammonium chloride with acrylic acids having a weight average molecular weight from about 50,000 to about 10,000,000 has the CTFA name Polyquaternium-22 and is sold under the trademark MERQUAT-280. Polyquaternium-6 is particularly preferred.

Other polymeric conditioners include cationic copolymers of methylvinylimidazolium chloride and vinyl pyrrolidone, sold commercially by BASF Aktiengesellschaft, West Germany under the trademark LUVIQUAT at three comonomer ratios, namely at ratios of 95/5, 50/50 and 30/70 methylvinylimidazolium chloride to polyvinylpyrrolidone. These copolymers at all three comonomer ratios have the CTFA name Polyquaternium 16. Polymeric conditioners also include cationic cellulosic polymers of hydroxyethyl cellulose reacted with epichlorohydrin and quaternized with trimethylamine, sold under the trademark POLYMER JR in various viscosity grades and molecular sizes by Union Carbide Corporation, Danbury, Conn. These series of polymers are named Polyquaternium 10 in the CTFA Dictionary. Also useful are quaternized copolymers of hydroxyethylcellulose and dimethyldimethylammonium chloride, having the CTFA name Polyquaternium-4, sold in varying molecular weights under the trademark CELQUAT by National Starch and Chemical Corporation, Bridgewater, N.J.

It is understood that a number of other cationic polymeric conditioning agents are commercially available and known that can also be used. The disclosure of the preferred cationic polymer is not intended to limit the scope of this invention.

Smaller molecule cationic non-polymeric conditioning agents can also be utilized herein. Exemplary small-molecule conditioning agents can include monofunctional or difunctional quaternary ammonium compounds, such as stearyldimethylbenzylammonium chloride, dimethyldi-(hydrogenated tallow)ammonium chloride, and the like. Non-polymeric conditioning agents can also include the quaternary ammonium salts of gluconamide derivatives, such as gamma-gluconamidopropyldimethyl-2-hydroxyethyl-ammonium chloride and minkamidopropyldimethyl-2-hydroxyethylammonium chloride identified respectively by the CTFA names Quaternium 22 and Quaternium 26. Details for the preparation of these materials are found in U.S. Pat. Nos. 3,766,267 and 4,012,398, respectively, and the materials are sold under the trademark CERAPHYL by Van Dyk & Co., Belleville, N.J. Also useful are bis-quaternary ammonium compounds which are dimers, such as 2-hydroxy propylene-bis-1,3-(dimethylstearyl ammonium chloride, designated the CTFA name, Hydroxypropyl Bisstearyldimonium chloride. The preparation of these and other bis-quat materials is described in U.S. Pat. No. 4,734,277, and such materials are sold under the trademark JORDAQUAT DIMER by Jordan Chemical Company, Folcroft, Pa.

Exemplary unquaternized polymers having tertiary amino nitrogen groups that become quaternized when protonated can include water-soluble proteinaceous quaternary ammonium compounds. Cocodimonium hydrolyzed animal protein, for example, is the CTFA name for a chemically-modified quaternary ammonium derivative of hydrolyzed collagen protein having from about 12 to about 18 carbons in at least one aliphatic alkyl group, a weight average molecular weight from about 2500 to about 12,000, and an isoionic point in a range from about 9.5 to about 11.5. This material and structurally related materials are sold under the trademarks CROQUAT and CROTEIN by Croda, Inc., New York, N.Y.

A number of cationic compounds, their manufacturers and general descriptions of their composition can be found in the CTFA Dictionary and in the *CTFA Cosmetic Ingredient Dictionary*, 3rd Ed., Supplement (1985), also published by the Cosmetic Toiletry and Fragrance Association, Inc. the pertinent disclosures of both are incorporated herein by reference. The name assigned to the ingredients by the CTFA or by the manufacturer will be used for convenience.

It is well known that substantive conditioning effects can be produced on relaxed hair when a no-base, no-lye cream base containing the polymeric quaternary nitrogen conditioning agent, Polyquaternium-6, as an ingredient is mixed with a non-conditioning activator. Such products have been commercialized by the assignee of this invention. However, it has now surprisingly been found that about half the amount of Polyquaternium-6 normally used in the hair relaxer can produce substantially equivalent substantive conditioning effects by incorporating the cationic polymer in a substantially liquid activator instead of in the cream base.

For example, a substantive conditioning effect was produced by a conditioning hair relaxer system prepared with a no-base, no-lye cream base mixed with conditioning activator containing sufficient Polyquaternium-6 to provide about 0.5 weight percent of the polymer in the hair relaxer applied to the hair. The substantive conditioning effect produced on the relaxed hair was judged equivalent to or greater than that produced by a conditioning hair relaxer system prepared by mixing a non-conditioning activator with a no-base, no-lye cream base containing sufficient Polyquaternium-6 to provide about 1 weight percent Polyquaternium-6 in the hair relaxer.

A conditioning activator of this invention can be prepared by methods known to those skilled in the art for preparing activators generally. The conditioning agent can be incorporated in the activator by dissolving it in the water along with the rest of the ingredients. Alternatively, the conditioning agent can be added directly to a completed or nearly completed activator after the organic salt is dissolved.

The cationic conditioning agent should not interfere with the stability of the guanidine carbonate or its ability to release sufficient free guanidine base to relax hair. A preferred embodiment of a conditioning activator encompassing the principles of this invention comprises, prior to admixture with a no-lye cream base about 20 to about 30 weight percent, preferably about 25 to about 28 weight percent, guanidine carbonate and about 0.05 to about 15 weight percent, preferably about 0.1 to about 10 weight percent, of a water-soluble cationic conditioning agent. Preferably the conditioning activator composition further includes water-soluble cosmetic adjuvants such as polyhydroxy compounds having from about 3 to about 6 carbon atoms and water-soluble derivatives thereof, thickening agents, metal-ion chelating agents and optionally preservatives, perfume and product colorants. Polyhydroxy compounds, such as propylene glycol, glycerine, sorbitol and water-soluble sorbitan derivatives are particularly preferred.

The pH of the conditioning activator is preferably about 11 to about 13, more preferably about 11.5 to about 12. The viscosity of the conditioning activator is preferably sufficiently liquid for relatively fast intimate mixing with a relatively stiff viscous highly alkaline cream base. But the liquidity of the activator should not thin the admixture to a runny state or conversely increase the viscosity of the admixture so that it becomes difficult to distribute through or remove from the hair.

The viscosity of the conditioning activator is preferably adjusted by including thickening agents, such as xanthan gum and like natural gum thickeners, or by including cationic polymers capable of thickening, such as Polyquaternium-4 and Polyquaternium-10.

It is recognized that a conditioning hair-relaxer system embodying the principles of this invention can be practiced by incorporating more than one cationic compound in the activator composition, or alternatively by including a portion of the total amount of cationic conditioning agent desired in the conditioning activator composition and the remaining amount in the no-base, no-lye cosmetic cream base. It is also recognized that the conditioning agent can be packaged as a liquid or a powder form in a separate container and dissolved in the activator just prior to mixing the activator with cream base for use. For simplicity, however, the conditioning agent is, preferably incorporated in the activator.

A particularly preferred conditioning activator, which is intended to be mixed at a ratio of one part by weight activator to about 3.6 parts by weight no-lye cream base, comprises on a dry solid basis of the total weight of the activator about 0.05 to about 5 weight percent Polyquaternium-6, about 27 to about 30 weight percent guanidine carbonate, about 0.1 to about 0.5 weight percent sorbitol and sufficient thickening agent dissolved in water along with sufficient metal-ion chelating agent, if necessary. Optionally, the conditioning activator can contain sufficient colorant for tinting the appearance of the composition as well as preservative and fragrance.

The chemical stability of guanidine carbonate was retained during storage aging of conditioning activators embodying the principles of this invention. Analysis of guanidine carbonate activity can be carried out after storage aging such activators at room temperature and at an elevated temperature of about 45 degrees C. (about 113 degrees F.) for about 90 days. Moreover, effective conditioning was still produced by such storage-aged activator when used in a hair relaxing system.

Preferably a kit for a conditioning hair relaxer system embodying the principles of this invention comprises at least two packages. For example, a first package can include an aqueous conditioning activator as previously described. A second package can include an aqueous no-base, no-lye cosmetic cream base containing an alkaline earth hydroxide and having a pH of from about 12 to about 14. The contents of the first and second packages are admixed to provide a conditioning no-base no-lye hair relaxer system just before use.

Alternatively, the kit can have the cationic conditioning agent separately contained as stated earlier. In such an embodiment, the conditioning activator can be prepared by dissolving the cationic conditioning agent with the contents of the first package containing the activator prior to mixing the contents of the first package with the contents of the second package. Alternatively, all or a part of the separately packaged conditioning agent can be mixed with the contents of the second package containing the cream base prior to mixing the cream with the activator. Preferably, the no-lye cosmetic cream base portion in either hair relaxer system is phase-stable as described below.

It has also now been found that aqueous highly alkaline cosmetic cream base compositions with relatively low amounts of non-water components can be formed which are phase-stable on ageing for a commercially useful lifetime The term "highly alkaline", as used herein, refers to a pH from about 12 to about 14, preferably to a pH from about 12.5 to about 13.8. This pH is achieved by the presence of a non-volatile inorganic alkaline material that is sufficiently water-soluble in the continuous water phase to provide a highly alkaline pH.

The term "phase-stable" as described above refers to the physical stability and not to the chemical stability of the individual non-alkaline ingredients against decomposition by or interaction with the alkaline material under highly alkaline conditions over a relatively long lifetime of the emulsified composition. As stated earlier, phase-stable compositions defined herein are cosmetic cream bases which do not visibly de-emulsify or separate on storage aging at ambient temperature for at least about four weeks or at about 45 degrees C. (about 113 degrees F.) for at least about 1 week. For purposes of illustrating this invention, the foregoing time period is considered indicative of a commercially useful lifetime in the field.

In actual practice, however, it has been surprisingly found that emulsion compositions prepared according to this invention with relatively low amounts of non-water components are relatively stiff viscous creams which remain phase-stable and viscous on storage aging as described above for periods of months to years. These compositions thereby provide products having concentrations of active ingredients that are substantially constant throughout their useful lifetimes.

The term "non-water components" refers to all co-emulsified ingredients, other than water. A "relatively low amount" means that the emulsion-forming ingredients and the alkaline material present as part or all of the hair-relaxing agent together make up not more than about 50 weight percent on a dry solids basis of the total weight of the cream composition. The term "relatively stiff viscous cream" as used herein defines an emulsion product having a Brookfield viscosity of about 100,000 to greater than about 900,000 centipoise (cps), as measured with a model RVT Helipath spindle No. TE rotating at 5 revolutions per minute (rpm) for one minute at about 25 degrees C. (about 77 degrees F.).

In the case of a no-base, no-lye cream base, the physical stability of the cream portion of the product does not interfere with the formation of the active hair relaxing agent when the no-lye cream base is mixed with an activator. For example, guanidine hydroxide can be formed in an admixture of a phase-stable cosmetic cream base containing calcium hydroxide and an activator containing guanidine carbonate. However, the stability of the phase-stable cosmetic cream base may eventually be overcome in the admixture by the presence of the free organic base, such as guanidine or guanidine hydroxide. Thus, a phase-stable no-lye cosmetic cream base convertible for use in a hair relaxer is preferably supplied in a separate container than the activator for a two-part hair relaxer kit.

A phase-stable cosmetic cream base for use directly as a no-base lye hair relaxer can contain a water-soluble alkaline caustic material which is capable of both bringing the pH of the composition to a value of about 12 to about 14, and acting as the sole hair relaxing agent. Alkali metal hydroxides, including sodium hydroxide, potassium hydroxide and lithium hydroxide may be used as the water-soluble alkaline caustic material. Sodium hydroxide is preferred and may be present in amounts from about 1 to about 3 weight percent of the total composition, preferably from about 1.5 to about 2.5 weight percent. Such a hair relaxer is typically supplied as a single product in a hair relaxer kit.

In compounding a phase-stable emulsion cosmetic cream base, the oil phase comprises the substantially anhydrous, lipophilic ingredients. This includes the oleaginous material, a primary lipophilic nonionic emulsifier and an auxiliary anionic emulsifier. The oil phase is co-emulsified with an alkaline water phase as described below.

The oleaginous material predominantly includes petrolatum, mineral oils and mineral jellies, but can also include lanolin, water-insoluble silicones and like unctuous emulsifiable materials. Particularly preferred is a petrolatum-mineral oil mixture where the petrolatum comprises at least about 50 weight percent, preferably between about 55 and about 65 weight percent, of the weight of this mixture.

Useful petrolatum is available in several grades based upon both viscosity, melting point and color. The Saybolt seconds universal viscosities (S.S.U) of these products range from between about 50 and about 90 (50/90) S.S.U. at 210 degrees F. Preferably, a colorless or "white" product having a Saybolt viscosity of about 55/75 S.S.U. at 210 degrees F. and melting points in the degree range of 135°-140° F. and 127°-137° F. are used. Preferably, a grade that meets the standards of the United States Pharmacopeia (U.S.P.) is used.

Mineral oils useful herein are preferably U.S.P. grade white oils. Preferably, a colorless or "white" oil is used having Saybolt viscosities at 100 degrees F. of about 50/350 S.S.U. and specific gravities at 77 degrees F. of about 0.822 to about 0.895 (0.822/0.895). The materials having Saybolt viscosities of about 50/60 S.S.U. at 100 degrees F. and specific gravities in the ranges 0.822/0.833 at 77 degrees F. are preferred. In addition, a mineral jelly compounded of white petrolatum, white mineral oil and wax may also be used as an oleaginous material in the compositions of this invention.

The oleaginous materials may be present at about 15 to about 35 weight percent, preferably at about 25 to about 30 weight percent. However, the percentage actually used in a product depends upon the desired product consistency. For example, where a no-lye cream base is desired, the consistency of the cream must permit it to be admixed with a liquid activator. The resulting mixture must produce a no-base hair-relaxer cream that is substantially free of lumps and that does not thin to a runny soft product.

For a no-base no-lye cream base composition, the oleaginous material preferably comprises a petrolatum-mineral oil mixture containing at least about 50 weight percent petrolatum and present at about 25 to about 30 weight percent of the total weight of the no-lye cream base.

The oleaginous material can include lipophilic-modified hectorite clay gellants. It has been surprisingly found, however, that unlike prior compositions, phase-stable, relatively stiff creams can be prepared with relatively low amounts of up to about 3 weight percent, preferably of up to about 2 weight percent, of these clay gellants.

Where present, lipophilic hectorite clay gellants are preferably incorporated in pre-gelled form for convenience, as they are known in the art to be difficult to prepare. Pre-gelled oleaginous products containing the above clay gellants are commercially designated by their manufacturer as mastergels.

The mastergels are comprised of hectorite clays modified with (1) a quaternary nitrogen-containing compound such as Stearalkonium chloride or Quaternium-18 which contains at least one long chain substituent having about 8 to about 20 carbon atoms on the quaternary nitrogen atom, (2) propylene carbonate, and (3) a non-polar organic liquid. Examples of such non-polar organic liquids include but are not limited to mineral spirits, mineral oil, glycerides, such as castor oil, a mixture of lanolin oil and isopropyl palmitate, and the like. [Stearalkonium chloride and Quaternium-18 are defined in the CTFA Dictionary at pages 299 and 267, respectively.]

Specific, useful lipophilic gellants which are commercially available as mastergels include: Bentone Gel MIO, comprised of mineral oil, propylene carbonate and Quaternium-18 hectorite; Bentone Gel CAO, comprised of propylene carbonate, castor oil and Stearalkonium hectorite; Bentone Gels SS71 and S130, comprised of mineral spirits (ligroin or petroleum spirits having a boiling range of about 318 degrees–400 degrees F.), propylene carbonate and Quaternium-18 hectorite; and Bentone Gel Lantrol, comprised of propylene carbonate, a mixture of lanolin oil (dewaxed lanolin) and isopropyl palmitate, and Stearalkonium hectorite. The above hectorite gellants may be individually used, may be interchanged, one for the other in a given composition, or may be mixed together in a composition.

The foregoing mastergels are commercially available from NL Chemical/NL Industries, Inc., Hightstown, N.J. According to that supplier's product brochures, these mastergels contain about 10 percent modified clay gellant, about 86.7 percent non-polar organic liquid and about 3.3 percent propylene carbonate.

Thus, the lipophilic-modified hectorite clay may be present in the no-lye cream base portion of a no-base hair relaxer of this invention from zero to up to about 3 weight percent, preferably up to about 2 weight percent, more preferably up to about 1 weight percent, of the total composition prior to admixture with activator.

Nonionic emulsifying agents useful as the primary emulsifier, are preferably emulsifying waxes that meet the standards of the National Formulary (N.F.) or British Pharmacopeia (B.P.) and can be either the non-self-emulsifying or the self-emulsifying type. The term "emulsifying wax" denotes solid nonionic emulsifiers known in the art that are prepared as a mixture of fatty alcohols having from about 12 to about 24 carbon atoms, preferably predominantly lipophilic fatty alcohols having from about 14 to about 20 carbon atoms. Self-emulsifying waxes are typically prepared with an auxiliary hydrophilic emulsifier present. The hydrophilic nonionic emulsifiers present in the primary nonionic emulsifier as part of the emulsifying wax are usually polyoxyethylene derivatives of fatty acid esters of sorbitol and sorbitol anhydride. Preferred are polysorbates which generally comprise mixtures of oleate or stearate esters condensed with ethylene oxide.

A preferred N.F. grade emulsifying wax is prepared from cetostearyl alcohol containing a polyoxyethylene derivative of a fatty acid ester of sorbitan. This material is known as Emulsifying Wax N.F. and is a creamy white, wax-like solid which is freely soluble in ether, chloroform, alcohol and most hydrocarbon solvents, but is insoluble in water. It melts at a temperature between 48 degrees and 52 degrees C., has a hydroxyl value between 178 and 192, an iodine value not more than 3.5, a saponification value not more than 14, and a pH (in a dispersion of 3 parts in 100 parts of water) between 5.5 and 7.0. Emulsifying Wax N.F. is commercially available from a number of suppliers. Exemplary and preferred materials are sold under the name POLAWAX by Croda, Inc., New York, N.Y.; and LIPO-WAX P by Lipo Chemicals, Inc., Paterson, N.J.

Other useful emulsifying waxes are commercially sold comprising balanced blends of lipophilic fatty alcohols (some distilled or double distilled) derived from fatty acids containing about 12 to about 24 carbon atoms and ethylene adducts thereof. Particularly preferred are emulsifying waxes containing about 14 to about 20 carbon atoms, more preferably about 16 to about 18 carbon atoms. Alternatively, the primary nonionic emulsifier can be a balanced blend of the individual lipophilic fatty alcohols, having about 14 to about 20 carbon atoms, more preferably about 16 to about 18 carbon atoms. Particularly useful fatty alcohols include cetyl alcohol, stearyl alcohol, tallow fatty alcohols and like saturated monovalent linear alcohols obtained from vegetable sources, animal oils and fats.

Particularly preferred are tallow fatty alcohols manufactured and sold under the trademark HYDRENOL D or DD by Henkel KGaA, West Germany. According to the manufacturer, these materials comprise zero-2 percent $C_{12}$; 3-7 percent $C_{14}$; 25-35 $C_{16}$; 60-70 percent $C_{18}$; and zero to 2 percent $C_{20}$ moieties; less than 1.2 percent hydrocarbons, less than 0.3 percent water; and has an acid value of less than 0.1; a saponification value of less than 1.2; an iodine value of less than 1; a hydroxyl value of 210-220; and solidifies in the range of 48°-52° degrees C. Another preferred nonionic emulsifier is a fatty alcohol mixture containing cetyl and stearyl alcohols sold under the trademark TA1618F by The Proctor & Gamble Company Industrial Chemicals Divisions, Cincinnati, Ohio.

In the practice of this invention, the primary nonionic emulsifying agent is generally present at about 3 to about 15 weight percent, preferably at about 5 to about 12, more preferably at about 6 to about 10.

Anionic emulsifiers may be illustrated by polyoxyethylene oleyl ether phosphates having about 3 to about 20 oxyethylene groups, sodium lauryl sulfate, and the stearic acid anion and the like. Polyoxyethylene (3) oleyl ether phosphate is particularly preferred. In compounding a phase-stable cream, an anionic emulsifier in substantially non-aqueous form is included in the oil phase at about 0.01 to about 1.0 weight percent, preferably at about 0.1 to about 0.5 weight percent of the total composition.

The water phase of the cream composition generally contains the relatively more water-soluble auxiliary emulsifiers, amphoteric or zwitterionic emulsifiers and hydrophilic nonionic emulsifiers as well as a polyhydroxy compound having about 3 to about 6 carbon atoms, and polymeric conditioning agent, where present. Amphoteric or zwitterionic emulsifiers that become anionic at alkaline pH are preferred. A zwitterionic emulsifier contains both cationic and anionic moieties in the same molecule and includes amphoteric surface active agents.

Suitable amphoteric surfactants include alkylamphocarboxyproprionates, and alkylamphoglycinates having mono- or di-carboxyl groups derived from fatty acids having about 10 to about 22 carbon atoms in the fatty alkyl chain. Particularly preferred is stearoamphoglycinate, the CTFA name for 2-heptadecyl-1-carboxymethyl-1-(2-hydroxyethyl)-2-imidazolinium chloride, sold under the tradename Miranol DM by the Miranol Chemical Company, Inc., South Brunswick (Dayton), N.J. Additional amphoteric or zwitterionic emulsifiers include the class of surface active agents having an aminopropionate structure, such as N-fatty alkyl beta propionic acid and alkali metal salts thereof. Commercial materials having lauryl, myristyl, coco and tallow fatty alkyl groups are sold commercially under the tradename DERIPHAT by General Mills Chemicals, Inc., Cosmedia Group, Minneapolis, Minn.

Amphoteric emulsifier can be present at about 0.01 to about 2 weight percent, preferably at about 0.1 to about 1, more preferably at about 0.2 to about 0.5 weight percent, dry solids basis.

Hydrophilic nonionic emulsifiers include polyoxyethylene derivatives of fatty acid esters of sorbitol and sorbitol anhydride; polyethylene glycol esters of fatty acids, polyoxyethylene ethers of fatty alcohols, polyethylene oxide-polypropylene oxide condensates and polyoxyethylene lanolin ethers, and the like. Particularly preferred is polyoxyethylene (75) lanolin.

Hydrophilic nonionic emulsifiers can be present at about 0.01 to about 8 weight percent preferably at about 0.5 to about 5 weight percent, more preferably at about 1 to about 3 weight percent.

The use of particular concentrations of the auxiliary emulsifiers can be varied as desired to keep the make up of the total of the non-components together, with the alkaline material at no more than about 50 weight percent of the total composition. It has been found beneficial to use about 0.05 to about 10 weight percent of auxiliary emulsifier, inclusive of the anionic emulsifier.

In such an embodiment where about 0.01 to about 1 weight percent anionic emulsifier is present in the oil phase, the remaining auxiliary emulsifier can comprise about 9 to about 9.99 weight percent of a mixture of a hydrophilic nonionic emulsifier, preferably polyoxyethylene (75) lanolin, and an amphoteric or zwitterionic emulsifier in the water phase, preferably stearoamphoglycinate.

Suitable polyhydroxy compounds include propylene glycol, glycerin, butylene glycol, hexylene glycol, sorbitol and the like. Particularly preferred is propylene glycol. The polyhydroxy compounds can be present at about 0.1 to about 10 weight percent, preferably at about 3 to about 8 weight percent. Sorbitol is generally preferred as a component of the activator solution for a no-lye hair relaxer.

When present in the cosmetic cream base, the polymeric conditioning agent is preferably a quaternary nitrogen polymer prepared by polymerizing a diallyldimethylammonium salt. This cationic polymer is present at about 0.05 to about 5 weight percent, more preferably at about 0.1 to about 2 weight percent.

The hair relaxer composition can also include cosmetic adjuvants, such as auxiliary emollients, auxiliary thickening agents, perfumes, preservatives, and product colorants present in the cosmetic cream base composition, in the activator, or in both.

In one relatively easy method aspect, inversion emulsification methods can be used to prepare a highly alkaline cosmetic cream base composition of this invention. As practiced, the substantially anhydrous components of the oil phase are mixed together, including the hectorite clay gellant when present, by heating and agitating the mixture at about 80 degrees C. (about 176 degrees F.) for about 30 minutes or until a substantially homogeneous uniform dispersion results.

In a separate vessel, the remaining non-water components, except sodium hydroxide when present, are mixed with water to form the water phase. This mixture is heated and agitated at about 80 degrees C. (about 176 degrees F.) for about 15 minutes or until a substantially uniform solution results.

The bulk portion of the water phase is then slowly added with agitation to the oil phase at a rate sufficient to effect inversion to oil-in-water emulsion. Agitation is continued thereafter for about 30 to about 45 minutes. The agitated mixture is then cooled to between about 45 to about 50 degrees C. (about 113 and 122 degrees F.) at which temperature aqueous (50 weight percent solution) sodium hydroxide, adjuvants, perfume and the like, if present, are added. The mixture is diluted to its final volume with deionized water if necessary. The mixture is then stirred, as necessary, for about an additional 15 minutes to ensure homogeneity, or until a relatively stiff viscous cream base results. The cream is then force cooled to about ambient temperature (about 25 degrees C. or about 72 degrees F.). On reaching ambient temperature, the mixture can be homogenized by conventional techniques, such as by ultrasonic mixing.

In another method aspect, the polyhydroxy compound can be withheld initially from the water phase in the foregoing method and added to the heated admixture of water and oil phase instead.

The preparation of a no-base lye-type hair relaxer creams, in which sodium hydroxide, for example, is intended to be the sole active hair-relaxing agent, is generally similar to that of a no-lye cream base, except for withholding the inclusion of the sodium hydroxide until the emulsion is formed and cooled to between about 45 and about 50 degrees C. (about 113 and 122 degrees F.).

In still another method aspect, a phase-stable, viscous, highly alkaline no-base no-lye cosmetic cream base composition of this invention can be prepared by a non-inversion emulsification method. As practiced, the water phase is prepared by dissolving inorganic alkaline material having an earth metal cation and the polyhydroxy compound in the available water by agitating the mixture at ambient room temperature for about 30 minutes or until a substantially homogeneous solution results. The term "available water" means all of the intended water content in the formula decreased by the amount of water contributed from ingredients supplied as aqueous solutions.

The resulting water solution is then heated to about 80 degrees C. (about 176 degrees F.). During this heating step, the auxiliary water-soluble amphoteric and water-soluble nonionic emulsifiers, and polymeric conditioning agent, if present, are gradually added and dissolved by mixing. The mixture is agitated at the foregoing elevated temperature until a substantially homogeneous water phase is obtained.

In a separate vessel, the oil phase is prepared as described earlier with the remaining anhydrous non-water components, including the hectorite clay gellant, when present. For this method embodiment, however, the heated oil phase is then added to the heated water phase, when both phases are each at about 80 degrees C. (about 176 degrees F.) and mixed by agitating until an emulsion having a substantially smooth, non-grainy appearance forms. The resulting smooth emulsion is then cooled to about 55 degrees C. (about 131 degrees F.) and perfumed, if desired, and then further cooled as described above to about ambient temperature and then, optionally, homogenized.

Cosmetic cream bases, especially no-base, no-lye cream bases, prepared according to the above procedures surprisingly are stiff viscous creams having a Brookfield viscosity of at least about 100,000 to greater than about 900,000 cps. Preferably, the viscosity is in a range of between about 150,000 to about 800,000, more preferably between about 200,000 to about 600,000. The creams maintain their viscosity even on accelerated ageing at about 45 degrees C. (about 113 degrees F.) as well as at ambient room temperature for as long as about 3 to about 6 months. Some compositions prepared by the methods described have remained phase-stable and viscous for several years, both at ambient room temperature and at elevated temperature.

When guanidine is intended to be the active water-soluble alkali hair-relaxing agent, the emulsified cream composition contains calcium hydroxide, or another alkaline earth hydroxide, and is blended with activator in proportions producing sufficient free guanidine or guanidine hydroxide to relax hair in an amount within the limits disclosed above.

It has been surprisingly found that an admixture comprised of about 3.5 to about 6 parts by weight of a phase-stable "no-lye" cosmetic cream base of this invention with one part by weight of activator provides improved hair straightening where the aqueous activator solution comprises guanidine carbonate at about 28 to about 30 weight percent, preferably about 29 weight percent, prior to admixture. The reason for the improved hair straightening effect is not fully understood.

Particularly preferred in this regard, is an activator including sorbitol at about 0.2 to about 0.5 weight percent and a natural gum thickening agent at about 0.1 to about 0.3 weight percent both calculated on a dry solids basis of the total weight of the activator.

When using the stable cosmetic cream bases of this invention in a no-base hair relaxer procedure, it is preferable that the person on whose head the compositions will be used (the model) not wash her (or his) hair for at least 24 hours prior to the relaxer treatment. This preference stems from the scalp protecting effect produced by the model's own sebum secretions. In addition, while washing the hair, slight physical damage can occur to the scalp which can become aggravated by the alkaline material in the relaxer.

The model's hair is divided into four portions as delineated by the areas separated when hypothetical lines are drawn from ear-to-ear and from nose-to-backbone. Starting with the rear portions, the relaxer cream is applied to the hair with the back or smooth side of a comb (opposite from the teeth). Care is taken to avoid putting the composition on the scalp and about ⅛-¼ inch of the root end (lower portion) of the hair shaft. This process takes about 8 minutes for treatment of all the model's hair.

Each portion of the hair is then physically smoothed with the comb back. At this time in the treatment, the scalp and lower portions of the hair shafts are contacted with the relaxer cream. The smoothing step helps to ensure adequate hair shaft penetration and softening by the relaxer and also puts tension on the hair to help in straightening the hair. The smoothing step is then repeated to facilitate straightening. The total time for smoothing (both the initial and the repeat steps) normally takes from about 5 to about 10 minutes, depending upon the hair length and thickness. Thus, at this point, the relaxer is on the head for about 13 to about 18 or about 20 minutes.

The relaxer is then thoroughly and rapidly removed from the hair by rinsing with water having a temperature of about 37 degrees C. (about 77 degrees F.). The rinsing step is followed by a shampooing with a non-alkaline shampoo. The shampoo is preferably buffered on the acid side of neutral at about pH 4 to 6 so that residual alkali left in the hair or on the scalp is neutralized. This shampooing is usually repeated two to three times.

After shampooing, the hair may be treated with a conditioner to improve wet combing and hair feel. When the conditioning relaxers of this invention are used, no extra conditioning step is needed. The hair may then be set and dried in a desired coiffure as is known in the art.

In effect, the highly alkaline no-lye cosmetic cream base compositions of this invention are of high water, low solids type. The following Examples illustrate highalkaline, phase-stable cream bases, conditioning activators and conditioning hair relaxer systems of this invention with generally preferred ingredients and methods of preparation, but are not intended to be limited thereby.

EXAMPLE 1

Phase Stable No-Lye Cream Base

The following compositions illustrate no-lye cream base compositions containing low amounts of clay gellant convertible for use as a guanidine based no-base hair relaxer by admixture with activator.

| Components | Weight Percent, Dry Solid Basis of Emulsified Cream Base | | | | | |
|---|---|---|---|---|---|---|
| | A | B | C | D | E | F |
| I. Oil Phase | | | | | | |
| Petrolatum (Note 1) | 15 | 15 | 15 | 15 | 15 | 15 |
| Mineral Oil (Note 2) | 12 | 10 | 12 | 10 | 10 | 12 |
| Emulsifying Wax N.F. (Note 3) | 8 | 9 | 8 | 7 | 9 | 9 |
| Polyoxyethylene (3) Oleylether phosphate | 0.25 | 0.25 | 0.25 | 0.25 | 0.25 | 0.25 |
| Modified Hectorite Clay Gellant (Note 4) | 2 | 2 | 2 | 2 | 2 | 1.5 |
| II. Water Phase | | | | | | |
| Water, deionized to 100 percent | Q.S. | Q.S. | Q.S. | Q.S. | Q.S. | Q.S. |
| Calcium hydroxide | 6.3 | 5 | 5 | 5 | 6 | 6 |
| Polymeric quaternary nitrogen conditioning agent (Note 5) | — | 1.2 | — | 1.2 | 1 | — |
| Amphoteric Emulsifier (Note 6) | 0.37 | 0.37 | 0.37 | 0.37 | 0.5 | 0.25 |
| Polyoxyethylene (75) lanolin (Note 7) | 1.5 | 1.5 | 1.5 | 1.5 | 1.5 | 1.5 |
| Propylene glycol | 5 | 5 | 5 | 5 | 6 | 4 |
| III. Perfume | — | — | — | Q.S. | — | — |

Note 1. White petrolatum having a melting point of 127/137 degrees F. and a Saybolt viscosity at 210 degrees F. of 60/80 S.U.S. may be used.
Note 2. White mineral oil having a Saybolt viscosity at 100 degrees F of 50/60 S.S.U. and a specific gravity in the range of 0.822/0.833 at 77 degrees F may be used.
Note 3. POLAWAX available from Croda, Inc., New York, NY or LIPOWAX P available from Lipo Chemicals, Inc., Peterson, NJ may be used.
Note 4. A modified hectorite clay gellant mastergel sold by NL Industries, Inc., Hightstown, NJ, under the trademarks Bentone Gel MIO, Bentone Gel CAO, Bentone Gel SS71, Bentone Gel S130 and Bentone Gel Lantrol may be used.
Note 5. A water-soluble quaternary nitrogen-containing polymer available from Calgon Corporation, Pittsburgh, PA, under the trademark Merquat 100 as a 40 percent active aqueous solution may be used assigned the CTFA name of polyquaternium-6.
Note 6. Preferably stearamphoglycinate available from the Miranol Chemical Company, Inc., South Brunswick, NJ, under the trademark Miranol DM as a 20-27 percent active aqueous paste.
Note 7. Available as 50 percent active in water under the trademark LANETO 50 from the R.I.T.A. Corporation, Crystal Lake, IL.

The components of the oil phase are placed together in a heatable container equipped with a propeller-type mixer, heated to about 80 degrees C. and mixed for about 30 minutes or until a substantially uniform dispersion is formed. In a separate heatable container, the water and remaining components of the water phase are placed and also provided with a mixer. This admixture is heated to about 80 degrees C. and mixed for about 15 minutes.

The water phase is then added slowly with mixing agitation to the oil phase while maintaining the temperature at about 80 degrees C. The resulting emulsion is maintained at this temperature under continued agitation for about 30 to about 45 minutes and is then cooled to between about 55 degrees C. and about 45 degrees C. at which point perfume, if present, is added. The emulsion is again mixed for about 15 minutes and allowed to cool to form a substantially smooth cream base at about 45 to about 35 degrees C. The cream base is then force cooled to about 25 degrees C., homogenized and packaged.

The cream bases are relatively stiff viscous compositions that do not separate into distinct phases on ageing. For example, Cream Bases A-D had Brookfield viscosities at 25 degrees C. (Model RVT spindle model No. TE at 5 rpm for 1 minute) of about 200,000 to about 350,000 cps. On ageing at ambient room temperature, their viscosities appeared to stabilize at about 350,000 to about 525,000 cps, typically at about 400,000 to about 480,000 cps.

The phase stability of Cream Base A was followed under accelerated ageing conditions at about 45 degrees C. for at least six months. No separation was observed.

EXAMPLE 2

Phase Stable No-Lye Cream Base

This example illustrates no-lye cream base compositions containing as the primary emulsifier, a mixture of fatty alcohols having about 16 to about 18 carbon atoms ($C_{16}$–$C_{18}$).

| Components | Weight Percent, Dry Solid Basis of Emulsified Cream Base | | | | |
|---|---|---|---|---|---|
| | G | H | I | J | P |
| I. Oil Phase | | | | | |
| Petrolatum (Note 1 above) | 15 | 15 | 20 | 15 | 15 |
| Mineral Oil (Note 2 above) | 10 | 10 | 14 | 10 | 10 |
| $C_{16}$–$C_{18}$ Fatty Alcohols (Note 8) | 9 | 9 | 7 | 8 | 9 |
| Polyoxyethylene (3) Oleylether phosphate | 0.25 | 0.1 | 0.5 | 0.25 | 0.25 |
| Modified Hectorite Clay Gellant (Note 4 above) | 2 | 2.1 | 0.1 | — | 2 |
| II. Water Phase | | | | | |
| Water, deionized to 100 percent | Q.S. | Q.S. | Q.S. | Q.S. | Q.S |
| Calcium hydroxide | 6.3 | 6.3 | 4 | 5.5 | 6.3 |
| Polymeric quaternary nitrogen conditioning agent (Note 5 above) | 1.2 | 1.2 | — | 1.2 | 1.2 |
| Amphoteric Emulsifier (Note 6 above) | 0.37 | 0.37 | 0.1 | 0.2 | 0.5 |
| Polyoxyethylene (75) lanolin (Note 7 above) | 1.5 | 1.5 | 1 | 1.5 | 1.5 |
| Propylene glycol | 5 | 5 | 8 | 5 | 5 |
| III. Perfume | Q.S. | — | Q.S. | Q.S. | Q.S. |

Note 8. A fatty alcohol mixture containing cetyl and stearyl alcohols sold under the trademark TA 1618F by Proctor & Gamble or a tallow fatty alcohol sold under the trademark HYDRENOL D by Henkel KGaA, Germany may be used.

The procedure of Example 1 is followed in preparing the compositions and in measuring Brookfield viscosity.

The Brookfield viscosity of Cream Base G is about 280,000 to about 350,000 cps, and that of Cream Base H is about 250,000 to about 400,000 cps. The viscosities of both creams bases stabilize on ageing at ambient temperature at between about 425,000 to about 500,000 within about a week.

EXAMPLE 3

Phase Stable No-Lye Cream Base

This example illustrates the preparation of a phase-stable composition, Composition P of Example 2 by non-inversion method. The procedure of Example 1 is followed for preparing the oil phase (I), mixing it for about 30 to about 45 minutes or until a substantially homogeneous dispersion forms except that the water phase is prepared as follows.

In a separate heatable container, equipped with a mixer, the water, propylene glycol and calcium hydroxide are placed and mixed together for about 30 minutes or until a substantially homogeneous solution is obtained. This admixture is then heated to about 80 degrees C. and, during this heating step, the remaining components of the water phase (II) are added. The water phase is mixed at this elevated temperature, about 15 minutes, preferably less, until a substantially homogeneous solution forms.

The heated oil phase is added to the heated water phase while both phases are each at the above elevated temperature. The admixture is maintained at this elevated temperature and mixed together until an emulsion forms having a smooth, non-grainy appearance. The resulting smooth emulsion is then cooled to between about 45 and about 55 degrees C. at which temperature perfume (III) if present, is added. The emulsion is then cooled to about 25 degrees C., homogenized and packaged. The emulsion is a relatively stiff viscous cream base that remains phase stable on storage aging.

EXAMPLE 4

Phase Stable No-Lye Cream Bases

This example illustrates no-lye cream bases that are stabilized using Emulsifying Wax as the primary emulsifier and no hectorite clay gellant, but are otherwise generally prepared following the procedure of Example 1.

| Components | Weight Percent, Dry Solid Basis of Emulsified Cream Base | | | | |
|---|---|---|---|---|---|
| | K | L | M | N | O |
| I. Oil Phase | | | | | |
| Petrolatum (Note 1 above) | 15 | 15 | 15 | 15 | 15 |
| Mineral Oil (Note 2 above) | 12 | 12 | 12 | 12 | 12 |
| Emulsifying Wax N.F. | 9 | 8 | 7 | 7 | 9 |
| Polyoxyethylene (3) Oleylether phosphate | 0.25 | 0.25 | 0.25 | 0.25 | 0.25 |
| II. Water Phase | | | | | |
| Water, deionized to 100 percent | Q.S. | Q.S. | Q.S. | Q.S. | Q.S. |
| Calcium hydroxide | 5 | 5 | 5 | 5 | 5 |
| Polymeric quaternary nitrogen conditioning agent (Note 5 above) | 1.2 | — | — | 1.2 | — |
| Amphoteric Emulsifier (Note 6 above) | 0.37 | 0.37 | 0.37 | 0.37 | 0.37 |
| Polyoxyethylene (75) lanolin (Note 7 above) | 1.5 | 1.5 | 1.5 | 1.5 | 1.5 |
| Propylene glycol | 5 | 5 | 5 | 5 | 5 |

The Brookfield viscosity of freshly prepared Cream K was about 240,000 cps to about 250,000 cps, increasing to between about 480,000 to about 950,000 cps on aging at ambient room temperature at about 2 to about 4 weeks.

The Brookfield viscosities of freshly prepared Creams L-O ranged between about 150,000 to about 300,000 cps and between about 350,000 and about 750,000 on aging at ambient room temperatures for about one week.

EXAMPLE 5

No-Base Hair Relaxer

Cream bases that are directly usable as a no-base hair relaxer can be prepared by substituting about 1 to about 2.5 weight percent sodium hydroxide in the formula for Cream A of Example 1 in place of calcium hydroxide.

In preparing this hair relaxer cream, the procedure of Example 1 is followed, except that the sodium hydroxide is withheld from the water phase. When the cream base has cooled to between about 50 and 45 degrees C., the sodium hydroxide is added, preferably as a concentrated aqueous solution, before the perfume. To ensure homogeneity the cream is stirred about another 15 minutes prior to adding the perfume.

EXAMPLE 6

Phase Stable No-Lye Cream Base

Cream Base G of Example 2 can be prepared in a commercial scale quantity following the general procedure of Example 1, except that propylene glycol is initially withheld from the water phase. After the water phase is been added and the heated emulsion reaches about 75 to about 80 degrees C., the propylene glycol is added while maintaining the temperature. A viscous cream base forms at between about 40 and about 35 degrees C.

EXAMPLE 7

No-Base No-Lye Hair Relaxer Cream

This example illustrates the conversion of no-lye cream base of this invention for use in a no-base no-lye hair relaxing procedure.

An aqueous activator (X) solution of guanidine carbonate was prepared containing about 28 to about 30 weight percent guanidine carbonate, about 0.2 to about 0.25 weight percent sodium alginate (as thickening agent) about 0.35 weight percent sorbitol (dry solids basis) and sufficient preservative.

One part by weight of the activator (X) was mixed with about 3.5 to about 3.7 parts by weight of Cream Base G of Example 2 to provide a hair relaxer cream. In commercial practice, a representative admixture of about 220 grams Cream Base G and about 60 g of the foregoing activator (X) containing about 29 weight percent guanidine carbonate was particularly preferred as a hair relaxer cream (HR-A).

Likewise Cream Base A of Example 1 can be converted to a hair relaxer (HR-B) by admixing one part by weight of activator (X) with about 3.7 to about 6 parts by weight Cream Base A to provide a hair relaxer varying from "super" to "regular" strength.

EXAMPLE 8

No-Base No-Lye Hair Relaxer

In salon tests, hair relaxer HR-A of Example 7 gave relaxing or straightening results that were equivalent to or superior to those obtained with a commercial no-base no-lye hair relaxer cream of comparable alkalinity stabilized with relatively high amounts of hectorite clay gellant in accordance with the teachings of U.S. Pat. Nos. 4,390,033 and 4,237,910.

A salon test was made with 50 volunteer persons having medium to coarse curly hair using a half-head comparison method. Each person received a hair relaxer procedure on one side with hair relaxer HR-A of Example 7 and on the opposite side with commercial hair relaxer (C) prepared using activator (X) of Example 7 containing about 29 to about 30 weight percent guanidine admixed with a commercial cream in the same proportions as for HR-A. The hair relaxing procedure was followed by applying a commercial neutralizing shampoo, using the same product on both sides.

The hair relaxing or straightening effect of hair relaxer HR-A was judged equivalent. The consistency of hair relaxer HR-A was also judged substantially more viscous than the hair relaxer C. This result was surprising because the commercial cream was phase-stabilized with a relatively high amount of modified hectorite clay gellant in excess of about 12 weight percent and contained substantially the same amount of calcium hydroxide. Additionally, the HR-A cream was equivalent to or preferred over the commercial hair relaxer for ease of distributing and smoothing through the hair, ease of rinsing, after-treatment feel of the wet and dry hair, sheen and manageability.

In another salon test, 52 persons having medium to coarse hair received a no-lye hair relaxer procedure with no-lye hair relaxer HR-A, of Example 7. The product was applied generally following known hair-relaxing procedures described earlier. The results again showed that the consistency of the hair relaxer HR-A, was very workable through the hair, judged not too firm or too soft, gave good relaxation results and made the hair soft, and easy to comb.

In a third salon test, five persons received a hair-relaxer procedure in a half-head comparison between a commercial no-base, no-lye cream and Cream Base H of Example 2. Each no-lye cream was mixed with the commercial activator supplied, which was generally similar to activator (X) of Example 7, and the resulting hair relaxer applied according to the manufacturer's directions.

The results showed that the consistency of the hair relaxer prepared with Cream Base H and its rinsing and after-treatment effect on the hair was substantially equivalent to the commercial product.

EXAMPLE 9

Activator compositions (Q-S)

The following compositions illustrate liquid conditioning activators containing guanidine carbonate and a polymeric or non-polymeric cationic conditioning agent. For convenience, the conditioning agent is identified by its CTFA name.

| Components | Weight Percent (Dry Solid Basis) |
| --- | --- |
| Guanidine carbonate | 27–30 |
| Cationic conditioning Agent (As identified below) | 0.1–15 |
| Sorbitol | 0.1–0.5 |
| Xanthan gum to desired viscosity | Q.S. |
| Chelating agent | Q.S. |
| Colorant to desired tint | Q.S. |
| Water, deionized, to 100 percent | Q.S. |
| pH | 11–12 |

| | Weight Percent (Dry Solid Basis) | | |
| --- | --- | --- | --- |
| Conditioning Agent | Q | R | S |
| Polyquaternium-6 (Note 5 above) | 2.4 | — | — |
| Polyquaternium-16 (Note 9) | — | 4.8 | — |
| Quaternium-22 (Note 10) | — | — | 12 |
| Approximate pH | 11.4 | 11.5 | 11.6 |

Note 9. A copolymer of methylvinylimidazolium chloride and vinyl pyrrolidone at a comonomer ratio of 95:5 available from BASF Aktiengesellschaft, Germany, under the trademark LUVIQUAT FC-905 as a 40 percent active aqueous solution.
Note 10. Gamma-gluconamidopropyldimethyl 2-hydroxyethyl ammonium chloride available from Van Dyk & Company, Inc., Belleville, NJ.

The viscosity of the activator was selected to maintain the activator sufficient liquid for easy admixing with the viscous cream yet retain sufficient viscosity in the admixture to keep the hair relaxer from dripping from the hair. The Brookfield viscosities of compositions Q and R, for example, are between about 100 and 300 cps.

In preferred commercial practice, about 60 grams of the conditioning activator is mixed with about 213 to about 218 grams of no-base no-lye cream composition to provide a conditioning hair relaxer system.

EXAMPLE 10

Conditioning Hair-Relaxer System

This comparative example illustrates two no-base, no-lye conditioning hair relaxer systems, A and B, each of which embodies the principles of this invention. In conditioning system A, the polymeric conditioning agent was Polyquaternium-6 present as a component of the activator portion, whereas in conditioning system B, the same polymeric conditioning agent was present as a component of the cosmetic cream base portion of a two-product hair relaxer kit.

Conditioning system A was prepared using the cosmetic cream base A of Example 1 and the conditioning activator Q of Example 9. Conditioning system B was prepared using the cosmetic cream base P of Example 2 and the non-conditioning activator X of Example 7. Each conditioning hair relaxer system was prepared by mixing one part by weight (about 60 grams) of the activator to about 3.6 parts by weight (about 213-218 grams) of the cosmetic cream base. Thus, the amount of Polyquaternium-6 present in the hair relaxer admixture applied to the hair was at about 0.5 weight percent in conditioning system A and at about 1 weight percent in conditioning system B.

The two conditioning hair relaxer systems were tested in salon studies generally following the half-head comparison method procedure of Example 8. One salon test was made with eleven volunteer persons and each hair relaxing procedure was followed by applying a commercial "non-conditioning" neutralizer shampoo, using the same product on both sides.

The hair straightening obtained showed that the presence of the polymeric conditioning agent in the activator did not interfere with the action of the active hair relaxing agent. The results also showed that the substantive conditioning effects produced on the relaxed hair by Polyquaternium-6 were substantially equivalent from conditioning system A and from conditioning system B. Thus, it was surprisingly noted that when Polyquaternium-6 was included in the activator portion of the kit instead of in the cream base portion, equivalent substantive conditioning was produced with about half the amount of that polymeric conditioning agent.

A second similar salon study was repeated using ten volunteer persons, except that the above conditioning system A was compared against a non-conditioning, no-base, no-lye hair relaxer system (system C). System C was prepared by admixing the no-base no-lye cream base A of Example 1 with the non-conditioning activator "X" of Example 7. The results showed that the substantive conditioning produced on the relaxer hair by conditioning system A was particularly discernible with regard to the tactile feel of the wet hair (soft) and the ease of wet combing (good) after shampooing with the non-conditioning neutralizing shampoo. In about one-third of the studies, the degree of hair relaxation obtained with the conditioning hair-relaxer system was preferred.

EXAMPLE 1

Conditioning Hair-Relaxer System

This example illustrates the use of another polymeric conditioning agent, Polyquaternium-16, as a component of the activator portion of a no-base, no-lye conditioning hair relaxer system. The procedure of the second salon study of Example 10 was followed with five volunteer persons, except that the conditioning hair-relaxer system (conditioning system D) was prepared by admixing the conditioning activator R of Example 9 with cream base A of Example 1 for comparison with system C. This hair relaxer admixture provided about 1.5 weight percent Polyquaternium-16 in the hair relaxer.

The conditioning system D provided some improvement in the ease of combing of the wet hair in two instances (representing 40 percent of the subject), and this improvement became more pronounced in three instances (representing 60 percent of the subjects) following the use of the neutralizing shampoo. The results also showed that the degree of relaxation and ease of rinsing of conditioning system D were substantially equivalent to those of the non-conditioning, no-base, no-lye system C.

A second similar study was made with fourteen volunteer persons, except that a commercial conditioning neutralizing shampoo containing the cationic polymer, Polyquaternium-7 was used to complete the process. The results again showed some substantive conditioning effect produced by the Polyquaternium-16 with regard to ease of wet combing of the relaxed hair prior to shampooing. Surprisingly, the conditioning shampoo desirably and considerably enhanced the substantive conditioning effect of Polyquaternium-16 on wet hair in five instances (representing about one-third of the subjects). This result also illustrates that a conditioning activator of this invention can be used in conjunction with post-relaxer conditioners or in conditioning hair relaxer system where extra conditioning is desired.

The present invention has been described generally and with respect to preferred embodiments. It will be understood that modifications and variations of the disclosed method and compositions may be made without departing from the spirit and scope of the novel concept of the present invention.

What is claimed is:

1. A substantially liquid conditioning activator for use in combination with a hair relaxer cream base which contains an alkaline material having an alkaline earth metal ion for producing a conditioning, no-base, no-lye hair relaxer system, said activator comprising a water solution of
   an effective base releasing amount of a water-soluble organic salt of a relatively strong organic base with an anion capable of being precipitated by an alkaline earth metal ion under highly alkaline conditions, and
   an effective hair conditioning amount of a water-soluble cationic conditioning agent,
   said activator, when subsequently mixed with said cream base containing said alkaline material releases said organic base in sufficient amount to effectively relax hair and produce a conditioned effect on said relaxed hair.

2. The activator of claim 1 wherein the organic base is selected from the group consisting of guanidine, N-methyl guanidine, dimethylaminoguanidine acetamidine, dimethylaminoamidine, aminoamidine and acetamide.

3. The activator of claim 1 wherein the organic base is guanidine.

4. The activator of claim 1 wherein the salt has an anion selected from the group consisting of carbonate, sulfate, sulfite, phosphate, fluoride, oxalate, tartrate, laurate and alginate.

5. The activator of claim 1 wherein the sale is guanidine carbonate.

6. The activator of claim 5 wherein the guanidine carbonate is present in an amount of about 20 to about 30 weight percent dry solids basis of the total weight of the activator prior to admixture.

7. The activator of claim 1 wherein the conditioning agent is selected from the group consisting of non-polymeric quaternary ammonium compounds, quaternized cationic polymers with at least one positively charged nitrogen atom in each periodically repeating unit of the polymer chain and copolymers thereof, unquaternized polymers having tertiary amino nitrogen groups which become quaternized when protonated under alkaline conditions and copolymers thereof.

8. The activator of claim 1 wherein the conditioning agent is present at about 0.5 to about 15 weight percent, dry solids basis of the total weight of the activator, prior to admixture.

9. The activator of claim 1 wherein the amount of conditioning agent provides about 0.01 to about 5 weight percent, dry solids basis of the total weight of the admixture.

10. The activator of claim 1 wherein the conditioning agent is a cationic polymer which is a homopolymer or copolymer of a dialkyldiallylammonium salt in which the alkyl group contains 1 to about 18 carbon atoms.

11. The activator of claim 1 wherein the conditioning agent is a cationic polymer which is a copolymer of a methylvinylimidazolinium salt and polyvinylpyrrolidone.

12. The activator of claim 1 further including water-soluble cosmetic adjuvants selected from the group consisting of polyhydroxy compounds having from about 3 to about 6 carbon atoms and derivatives thereof, thickening agents, metal-ion chelating agents, and optionally preservatives, perfume and product colorants.

13. The activator of claim 12 wherein the polyhydroxy compound is selected from the group consisting of sorbitol, glycerine, propylene glycol, sorbitol and water-soluble sorbitan derivatives.

14. A substantially liquid activator for a conditioning no-lye hair relaxer system, the activator comprising a water solution of:
 about 20 to about 30 weight percent of guanidine carbonate, and
 about 0.05 to about 15 weight percent of a water-soluble cationic conditioning agent,
 the activator, when admixed with a no-lye cream base containing an alkaline material with an alkaline earth metal cation, releasing sufficient guanidine base in the admixture to effectively relax hair and producing a conditioned effect on the relaxed hair.

15. The activator of claim 14 further including water-soluble cosmetic adjuvants selected from the group consisting of polyhydroxy compounds having from about 3 to about 6 carbon atoms and water-soluble derivatives thereof, thickening agents, metal-ion chelating agents, and optionally preservatives, perfume and colorants.

16. The activator of claim 14 wherein the conditioning agent is a cationic polymer.

17. The activator of claim 16 wherein the cationic polymer is a homopolymer or copolymer of a dialkyldiallylammonium salt or derivative thereof in which the alkyl group is methyl or ethyl.

18. The activator of claim 16 wherein the cationic polymer is Polyquaternium-6 present at about 0.01 to about 5 weight percent, dry solids basis of the total weight of the admixture.

19. The activator of claim 16 wherein the cationic polymer is a copolymer of methylvinylimidazolinium salt and polyvinylpyrrolidone.

20. The activator composition of claim 16 wherein the cationic polymer is Polyquaternium 16 present at about 0.01 to about 5 weight percent dry solids basis of the total weight of the admixture.

21. A conditioning hair relaxer system in at least two packages comprising:
 a first package containing a substantially liquid conditioning activator comprising a water solution of an effective base releasing amount of a water-soluble organic salt of a relatively strong organic base, said salt having an anion capable of being precipitated by an alkaline earth metal ion under highly alkaline conditions, in combination with an effective hair conditioning amount of a water-soluble cationic conditioning agent, and
 a second package containing an aqueous no-base, no-lye hair relaxer cream base containing an alkaline material with an alkaline earth metal cation, said cream base having a pH of about 12 to about 14,
 whereby for use said first and second packages are admixed to produce a conditioning no-lye hair relaxer system.

22. The hair relaxer system of claim 21 wherein the organic salt in the activator is guanidine carbonate and the alkaline material in the cream base is calcium hydroxide.

23. The hair relaxer system of claim 21 wherein the cationic conditioning agent in the activator is selected from the group consisting of non-polymeric quaternary ammonium compounds, quaternized cationic polymers with at least one positively charged nitrogen atom in each periodically repeating unit of the polymer chain and copolymers thereof, unquaternized polymers having tertiary amino nitrogen groups that become quaternized when protonated under highly alkaline conditions and copolymers thereof.

24. The hair relaxer system of claim 21 wherein the activator in the first package contains guanidine carbonate present at about 20 to about 30 weight percent and the conditioning agent is a cationic polymer present in an amount of from about 0.05 to about 15 weight percent, each calculated on a dry solids basis of the total weight of the activator.

25. The hair relaxer system of claim 24 wherein the cationic polymer is a homopolymer or copolymer of a dialkyldiallylammonium salt in which the alkyl group is methyl or ethyl.

26. The hair relaxer system of claim 24 wherein the cationic polymer is Polyquaternium-6 present at about 0.01 to about 5 weight percent dry solids basis of the total weight of the admixture.

27. The hair relaxer system of claim 24 wherein the cationic polymer is a copolymer of methylvinylimidazolinium salt and polyvinylpyrrolidone.

28. The hair relaxer system of claim 23 wherein the cationic polymer is Polyquaternium 16 present at about 0.01 to about 5 weight percent dry solids basis of the total weight of the admixture.

29. The hair relaxer system of claim 21 wherein the no-base, no-lye cream base in the second package is an oil-in-water emulsion which, prior to admixing, is stable to phase separation on storage aging, said emulsion containing no more than about 50 weight percent of non-water components on a dry solids basis of the total weight of the cream base composition, the non-water components consisting essentially of about 15 to about 35 weight percent of a lipophilic oleaginous material, zero to about 2 weight percent of a lipophilic modified hectorite clay gellant, about 3 to about 15 weight percent of a primary nonionic emulsifier comprising a mixture of fatty alcohols each having about 12 to about 24 carbon atoms in its fatty carbon chain, about 0.05 to about 10 weight percent of an auxiliary emulsifier comprising a hydrophilic nonionic emulsifier, an anionic emulsifier, and an amphoteric or zwitterionic emulsifier, about 0.1 to about 10 weight percent of a water-soluble polyhydroxy compound having 3 to about 6 carbon atoms, zero to about 5 weight percent polymeric cationic conditioning agent and about 0.1 to about 10 weight percent calcium hydroxide co-emulsified in water.

30. The no-lye hair relaxer system of claim 21 wherein the activator solution further includes a water-soluble polyhydroxy compound having about 3 to about 6 carbon atoms or water-soluble derivative thereof, a thickening agent, a metal-ion chelating agent and optionally preservatives, colorant and perfume.

31. The no-lye hair relaxer resulting from the admixture of the first and second package of the hair relaxer system of claim 21 wherein the cationic conditioning agent in the activator is Polyquaternium-6 present in the admixture at from about 0.01 to about 5 weight percent calculated on a dry solids basis of the total weight of the admixture.

32. The no-lye hair relaxer resulting from the admixture of the first and second package of the hair relaxer system of claim 21 wherein the cationic conditioning agent in the activator is Polyquaternium-16 present at from about 0.01 to about 5 weight percent calculated on a dry solids basis of the total weight of the admixture.

33. The no-lye hair relaxer resulting from the admixture of the first and second package of the hair relaxer system of claim 30.

34. A method for conditioning and relaxing hair comprising the steps of:
(a) preparing a conditioning no-base, no-lye hair relaxer by admixing the first and second packages of claim 30;
(b) applying to the hair an effective amount of the hair relaxer so prepared in step (a);
(c) smoothing the so applied hair relaxer on said hair and leaving the hair relaxer on said hair for a time sufficient to achieve adequate hair softening and hair relaxing; and
(d) removing said hair relaxer from said hair.

35. A method for conditioning and relaxing hair comprising the steps of:
(a) admixing the activator of claim 1 with a no-base, no-lye cream base to produce a conditioning hair relaxer;
(b) applying to the hair an effective amount of the hair relaxer so produced in step (a);
(c) smoothing the so applied hair relaxer on said hair and leaving the hair relaxer on said hair for a time sufficient to achieve adequate hair softening and hair relaxing; and
(d) removing said hair relaxer from said hair.

36. A method for conditioning and relaxing hair comprising the steps of:
(a) admixing the contents of the first package and the second package of the hair relaxer system of claim 29 to produce a conditioning, no-base, no-lye hair relaxer;
(b) applying to the hair an effective amount of the hair relaxer so produced in step (a);
(c) smoothing the so applied hair relaxer on said hair and leaving the hair relaxer on said hair for a time sufficient to achieve adequate hair softening and hair relaxing; and
(d) removing said hair relaxer from said hair.

37. A method for conditioning and relaxing hair comprising the steps of:
(a) admixing the first and second package of the hair relaxer system of claim 32 to produce a conditioning hair relaxer;
(b) applying to the hair an effective amount of said hair relaxer so produced in step (a);
(c) smoothing the so applied hair relaxer on said hair and leaving the hair relaxer on said hair for a time sufficient to achieve adequate hair softening and hair relaxing; and
(d) removing said hair relaxer from said hair.

38. The method of claim 37 further including the step of washing the hair with a shampoo containing a polymeric conditioning agent.

39. A kit for no-lye hair relaxer system containing in at least one package the activator of claim 1.

40. In a kit for a conditioning hair relaxer system comprising at least a no-lye cream base portion in one package and an activator portion in a second package, the improvement comprising including a cationic conditioning agent dissolved in the activator prior to admixing the activator with the cream base.

41. The kit of claim 40, wherein the cationic conditioning agent is selected from the group consisting of non-polymeric quaternary ammonium compounds, quaternized cationic polymers with at least one positively charged nitrogen atom in each periodically repeating unit of the polymer chain and copolymers thereof, unquaternized polymers having tertiary amino nitrogen groups which become quaternized when protonated under alkaline conditions and copolymers thereof.

42. The kit of claim 40, wherein the cationic conditioning agent dissolved in the activator is a cationic polymer.

43. The kit of claim 40, wherein the cationic conditioning agent is separately contained in a third package and is intended to be dissolved in the activator prior to use.

44. The kit of claim 43, wherein a portion of the cationic conditioning agent is dissolved in the cream base and in the activator.

45. The kit of claim 40, wherein the cationic conditioning agent is Polyquaternium-6.

46. The kit of claim 40, wherein the cationic conditioning agent is Polyquaternium-16.

* * * * *

UNITED STATES PATENT AND TRADEMARK OFFICE
CERTIFICATE OF CORRECTION

PATENT NO. : 5,077,042

DATED : December 31, 1991

INVENTOR(S) : Darkwa, et al

It is certified that error appears in the above-identified patent and that said Letters Patent is hereby corrected as shown below:

Col. 4, lines 45, 46, insert hyphen as follows --cat-ionic--

Col. 5, line 67, change the word "art" to read --part--

Col. 7, lines 49, 50, insert hyphen as follows --di-methylaminoguanidine--

Col. 11, lines 17, 18, insert hyphen as follows --propyl-ene--

Col. 14, lines 52, 53, insert hyphen as follows --propyl-ene--

Col. 25, line 64, change "1" to -- 11 --

Col. 30, line 34, insert --a-- before the word "no-lye"

Signed and Sealed this

Twenty-eighth Day of July, 1992

Attest:

DOUGLAS B. COMER

Attesting Officer

Acting Commissioner of Patents and Trademarks